United States Patent
Hochberg et al.

(10) Patent No.: US 7,315,679 B2
(45) Date of Patent: Jan. 1, 2008

(54) SEGMENTED WAVEGUIDE STRUCTURES

(75) Inventors: Michael J. Hochberg, Pasadena, CA (US); Tom Baehr-Jones, Pasadena, CA (US); Chris I. Walker, Pasadena, CA (US); Jeremy Witzens, Pasadena, CA (US); Lawrence C. Gunn, Altadena, CA (US); Axel Scherer, Laguna Beach, CA (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 11/146,940

(22) Filed: Jun. 7, 2005

(65) Prior Publication Data
US 2006/0233504 A1  Oct. 19, 2006

Related U.S. Application Data

(60) Provisional application No. 60/577,905, filed on Jun. 7, 2004.

(51) Int. Cl.
G02B 6/10 (2006.01)

(52) U.S. Cl. .................................. 385/129
(58) Field of Classification Search .............. None
See application file for complete search history.

(56) References Cited

U.S. PATENT DOCUMENTS

| 3,462,211 | A | 8/1969 | Nelson et al. |
| 3,634,788 | A | 1/1972 | Craven |
| 3,970,364 | A | 7/1976 | Gerson et al. |
| 3,976,358 | A | 8/1976 | Thompson |
| 4,420,873 | A | 12/1983 | Leonberger et al. |
| 4,669,086 | A | 5/1987 | Kaede et al. |
| 4,728,167 | A | 3/1988 | Soref et al. |
| 4,776,655 | A | 10/1988 | Robertson et al. |
| 4,787,691 | A | 11/1988 | Lorenzo et al. |
| 4,857,973 | A | 8/1989 | Yang et al. |
| 4,874,216 | A | 10/1989 | Utaka et al. |
| 4,877,299 | A | 10/1989 | Lorenzo et al. |
| 4,956,682 | A | 9/1990 | Ohmaka et al. |

(Continued)

FOREIGN PATENT DOCUMENTS

EP  0 726 477 A2  8/1996

(Continued)

OTHER PUBLICATIONS

Baehr-Jones et al. "High-Q ring resonators in thin silicon-on-insulator". American Institue of Physics, vol. 85, No. 16, Oct. 18, 2004. pp. 3346-3347.

(Continued)

*Primary Examiner*—Michelle Connelly-Cushwa
*Assistant Examiner*—Chris Chu
(74) *Attorney, Agent, or Firm*—Knobbe, Martens, Olson & Bear LLP

(57) ABSTRACT

Various embodiment comprise silicon-on-insulator waveguide designs that simultaneously achieve both high optical confinement, low-loss, and provide for electrical connections. In certain embodiments, high index contrast waveguides comprise a central elongate waveguide portion and a segmented portion comprising a single thin layer of Silicon-On-Insulator that achieves both high optical confinement and minimal insertion loss. Other devices, such as chemical and biological sensors, and optical elements may also be fabricated.

30 Claims, 9 Drawing Sheets

U.S. PATENT DOCUMENTS

| | | | |
|---|---|---|---|
| 4,958,898 A | 9/1990 | Friedman et al. | |
| 4,999,686 A | 3/1991 | Autier et al. | |
| 5,001,523 A | 3/1991 | Lomashevich et al. | |
| 5,003,359 A | 3/1991 | Abeles | |
| 5,033,812 A | 7/1991 | Yoshida et al. | |
| 5,048,907 A | 9/1991 | Wickman et al. | |
| 5,061,030 A | 10/1991 | Miyamoto et al. | |
| 5,078,516 A | 1/1992 | Kapon et al. | |
| 5,101,459 A | 3/1992 | Sunagawa | |
| 5,109,464 A | 4/1992 | Munowitz et al. | |
| 5,125,065 A | 6/1992 | Stoll et al. | |
| 5,132,843 A | 7/1992 | Aoyama et al. | |
| 5,146,513 A | 9/1992 | Inoue et al. | |
| 5,148,507 A | 9/1992 | Tanisawa | |
| 5,199,092 A | 3/1993 | Stegmueller | |
| 5,200,939 A | 4/1993 | Nishiwaki et al. | |
| 5,222,162 A | 6/1993 | Yap et al. | |
| 5,225,740 A | 7/1993 | Ohkawa | |
| 5,227,701 A | 7/1993 | McIntyre | |
| 5,303,319 A | 4/1994 | Ford et al. | |
| 5,314,107 A | 5/1994 | d'Aragona et al. | |
| 5,329,601 A | 7/1994 | Nakamura | |
| 5,347,601 A | 9/1994 | Ade et al. | |
| 5,363,457 A | 11/1994 | Falt et al. | |
| 5,436,991 A | 7/1995 | Sunagawa et al. | |
| 5,459,807 A | 10/1995 | Doumuki et al. | |
| 5,491,768 A | 2/1996 | Chan | |
| 5,534,824 A | 7/1996 | Nalos et al. | |
| 5,546,494 A | 8/1996 | Eda | |
| 5,613,020 A | 3/1997 | Uchida et al. | |
| 5,625,725 A | 4/1997 | Nakano et al. | |
| 5,625,729 A | 4/1997 | Brown | |
| 5,654,818 A | 8/1997 | Yao | |
| 5,682,455 A | 10/1997 | Kovacic et al. | |
| 5,684,817 A | 11/1997 | Houdre et al. | |
| 5,703,989 A | 12/1997 | Khan et al. | |
| 5,710,849 A * | 1/1998 | Little et al. | 385/50 |
| 5,737,474 A | 4/1998 | Aoki et al. | |
| 5,742,433 A | 4/1998 | Shiono et al. | |
| 5,745,630 A | 4/1998 | Vawter et al. | |
| 5,759,453 A | 6/1998 | Kato | |
| 5,784,400 A | 7/1998 | Joannopoulos et al. | |
| 5,841,931 A | 11/1998 | Foresi et al. | |
| 5,854,866 A * | 12/1998 | Leonard | 385/39 |
| 5,889,898 A | 3/1999 | Koren et al. | |
| 5,908,305 A | 6/1999 | Crampton et al. | |
| 5,917,195 A | 6/1999 | Brown | |
| 5,917,981 A | 6/1999 | Kovacic et al. | |
| 5,920,662 A | 7/1999 | Hinkov | |
| 5,930,437 A * | 7/1999 | Nakai et al. | 385/129 |
| 5,955,749 A | 9/1999 | Joannopoulos et al. | |
| 6,052,495 A | 4/2000 | Little et al. | |
| 6,055,342 A | 4/2000 | Yi et al. | |
| 6,101,300 A | 8/2000 | Fan et al. | |
| 6,108,464 A | 8/2000 | Foresi et al. | |
| 6,134,369 A | 10/2000 | Kurosawa | |
| 6,151,430 A | 11/2000 | Traver, Jr. et al. | |
| 6,175,671 B1 | 1/2001 | Roberts | |
| 6,195,187 B1 | 2/2001 | Soref et al. | |
| 6,229,947 B1 | 5/2001 | Vawter et al. | |
| 6,243,517 B1 | 6/2001 | Deacon | |
| 6,261,525 B1 | 7/2001 | Minaee | |
| 6,278,822 B1 | 8/2001 | Dawnay | |
| 6,285,813 B1 | 9/2001 | Schultz et al. | |
| 6,374,001 B1 | 4/2002 | Bozeat et al. | |
| 6,396,984 B1 | 5/2002 | Cho et al. | |
| 6,400,490 B1 | 6/2002 | Hosoi | |
| 6,411,752 B1 | 6/2002 | Little et al. | |
| 6,466,342 B1 | 10/2002 | Frigo et al. | |
| 6,507,681 B1 | 1/2003 | Kowalczyk et al. | |
| 6,549,685 B2 | 4/2003 | Marks et al. | |
| 6,614,977 B2 | 9/2003 | Johnson et al. | |
| 6,631,225 B2 | 10/2003 | Lee et al. | |
| 6,633,696 B1 | 10/2003 | Vahala et al. | |
| 6,636,668 B1 | 10/2003 | Al-hemyari et al. | |
| 6,731,846 B2 | 5/2004 | Hosomi et al. | |
| 6,734,453 B2 | 5/2004 | Atanackovic et al. | |
| 6,751,368 B2 | 6/2004 | Lim et al. | |
| 6,759,675 B2 | 7/2004 | Csutak et al. | |
| 6,768,855 B1 | 7/2004 | Bakke et al. | |
| 6,801,702 B2 * | 10/2004 | Day | 385/130 |
| 6,831,938 B1 * | 12/2004 | Gunn, III | 372/92 |
| 6,834,152 B2 | 12/2004 | Gunn et al. | |
| 6,839,488 B2 | 1/2005 | Gunn | |
| 6,895,148 B2 | 5/2005 | Gunn | |
| 6,917,727 B2 | 7/2005 | Gunn et al. | |
| 6,961,490 B2 * | 11/2005 | Maisenhoelder et al. | 385/37 |
| 2002/0031321 A1 | 3/2002 | Lee et al. | |
| 2002/0057720 A1 | 5/2002 | Nomura et al. | |
| 2002/0081055 A1 | 6/2002 | Painter et al. | |
| 2002/0094150 A1 | 7/2002 | Lim et al. | |
| 2002/0094183 A1 | 7/2002 | Wu et al. | |
| 2002/0164118 A1 | 11/2002 | Paddon et al. | |
| 2002/0164129 A1 | 11/2002 | Jackson | |
| 2002/0164143 A1 | 11/2002 | Csutak et al. | |
| 2003/0002766 A1 * | 1/2003 | Pruneri et al. | 385/2 |
| 2003/0031446 A1 | 2/2003 | Gao et al. | |
| 2003/0040134 A1 | 2/2003 | Deliwala | |
| 2003/0068151 A1 | 4/2003 | Gunn et al. | |
| 2003/0174945 A1 * | 9/2003 | Fried et al. | 385/37 |
| 2003/0190107 A1 | 10/2003 | Walker | |
| 2004/0022474 A1 | 2/2004 | Lim et al. | |
| 2004/0037503 A1 * | 2/2004 | Hastings et al. | 385/37 |
| 2004/0076362 A1 | 4/2004 | Wong et al. | |

FOREIGN PATENT DOCUMENTS

| | | |
|---|---|---|
| EP | 0 751 409 A2 | 1/1997 |
| GB | 2 243 241 A | 10/1991 |
| JP | 63-106605 | 5/1988 |
| JP | 2001-4877 | 1/2001 |
| JP | 06-301934 | 10/2003 |
| WO | WO 02/082134 A1 | 10/2002 |
| WO | WO 02/082146 A1 | 10/2002 |
| WO | WO 03/107051 | 12/2003 |

OTHER PUBLICATIONS

Maune et al. "Electrically tunable ring resonators incorporating nematic liquid crystals as cladding layers". American Institue of Physics, vol. 83, No. 23, Dec. 8, 2003. pp. 4689-4691.

Weissman et al. "Modes of Periodically Segmented Waveguides". Journal of Lightwave Technology. vol. 11, No. 11, Nov. 1993. pp. 1831-1838.

Weissman et al. "Periodically Segmented Waveguides in Ti:LiNbo3". Optical Society of America, vol. 19, No. 21, Nov. 1, 1994. , pp. 1732-1734.

Weissman "Evanescent field sensors with periodically segmented waveguides". Applied Optics, vol. 36, No. 6, Feb. 20, 1997. pp. 1218-1222.

Weissman et al. "2-D Mode tapering via tapered channel waveguide segmentation". Electronics Letters, vol. 28, No. 16, Jul. 30, 1992. pp. 1514-1516.

J.D. Joannopoulos, R.D. Meade, and J.N. Winn, *Photonic Crystals* Princeton Univ. Press, Princeton, 1995 2. A. Taflove and S.C. Hagness, pp. 38-45 and pp. 112-116.

* cited by examiner

SEGMENTED WAVEGUIDE STRUCTURES

PRIORITY APPLICATION

This application claims priority under 35 U.S.C. § 119(e) from U.S. Provisional Patent Application Ser. No. 60/577,905, entitled "Segmented Waveguides in Thin Silicon on Insulator" and filed Jun. 7, 2004, which is hereby incorporated by reference herein in its entirety.

STATEMENT REGARDING FEDERALLY SPONSORED R&D

This invention was made with U.S. Government support under contract No. N00421-02-D-3223 awarded by the Naval Air Warfare Center Aircraft Division. The U.S. Government has a nonexclusive paid-up license in this invention.

BACKGROUND

1. Field of the Invention

The present invention is directed to waveguides, and more particularly, to waveguide structures incorporating a plurality of laterally extending segments.

2. Description of the Related Art

Low loss single-mode waveguides in thin Silicon-On-Insulator (SOI) have been demonstrated. Such waveguides may comprise, for example, a patterned silicon pathway formed on a silicon dioxide layer that is formed over a substrate. Light is substantially guided within the patterned silicon pathway.

Advantageously, these waveguides can be substantially thin. The thin geometry is helpful in obtaining high field concentrations in the waveguide cladding. Intense field concentrations in the cladding may be useful, for example, in the construction of sensors where interactions of the cladding with external stimulus perturb the propagation of light in the waveguide. The stimulus can thereby be sense by monitoring the optical output of the waveguide.

One of the outstanding problems of this geometry, however, is the difficulty of establishing an electrical contact with the waveguide without causing large losses in the optical mode. This problem is particularly troublesome when a DC or RF electrical field is to be applied directly to the waveguiding region. Such an applied electrical field can be used, for instance, to induce modulation through an electrically controllable index shift in the cladding; see e.g., B. Maune, R. Lawson, C. Gunn, A. Scherer, L. Dalton, "Electrically tunable ring resonators incorporating nematic liquid crystals as cladding layers," Applied Physics Letters 83, 4689-4691 (2003). To provide single mode propagation, the waveguides are particularly small. In general, a tradeoff exists between establishing good electrical contact, which often requires the use of a metal or a highly doped semiconductor region in close proximity to the optical mode, and providing a low-loss waveguide. If, for instance, a metal contact is placed directly onto a high-index-contrast silicon-on-insulator waveguide, with a mode that is less than 1 micron FWHM, the optical losses associated with that metal will be substantially large. The challenge is electrically contacting a compact, high index contrast optical waveguide without inducing large optical losses.

SUMMARY

One embodiment of the invention comprises a waveguide structure for supporting an optical mode having a wavelength, $\lambda$. The waveguide structure comprises an elongate waveguide portion, a plurality of segments extending from the elongate waveguide portion, and cladding disposed about the central elongate waveguide portion. The plurality of segments has a periodicity on the order of the wavelength, $\lambda$. In some embodiments, for example, the plurality of segments has a periodicity between about 0.1 and 3 times the wavelength, $\lambda$, or between about 0.1 and 2 times the wavelength, $\lambda$.

Another embodiment of the invention comprises a high index contrast waveguide structure for propagating a wavelength, $\lambda$, comprising an elongate waveguide portion and a plurality of segments extending from the elongate waveguide portion. The plurality of segments have periodicity so as to produce coherent scattering and reduce reflection. The high index waveguide structure further comprises cladding disposed about the elongate waveguide portion. The elongate waveguide portion and the cladding have sufficiently high index contrast so as to support an optical mode having a full width half maximum intensity having a width of about twice the wavelength, $\lambda$, or less. In one embodiment, for example, the width of the full width half maximum intensity is about 3 micrometers or less.

Another embodiment of the invention comprises a waveguide structure for supporting propagation of an optical mode having a wavelength, $\lambda$, comprising an elongate waveguide portion, a plurality of segments extending from the elongate waveguide portion, and cladding disposed about the central elongate waveguide portion, wherein the plurality of segments has a period of less than about 10 times the wavelength, $\lambda$. In some embodiments, for example, the plurality of segments has a period of no more than about 5 times the wavelength, $\lambda$. In other embodiments, the plurality of segments has a period no more than about 3 times the wavelength, $\lambda$. Other embodiments are possible.

BRIEF DESCRIPTION OF THE DRAWINGS

Preferred embodiments of the present invention are described below in connection with the accompanying drawings.

DETAILED DESCRIPTION OF CERTAIN PREFERRED EMBODIMENTS

Figure 1:
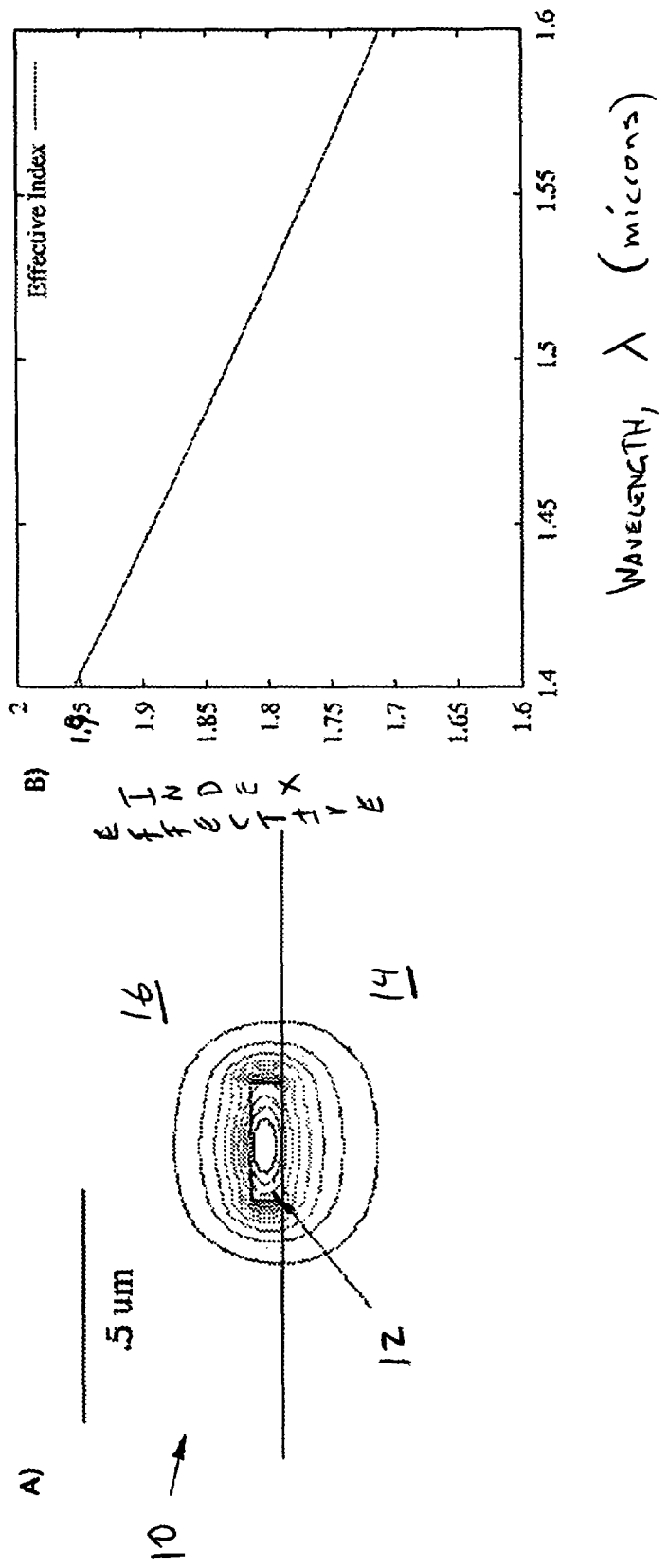
FIG. 1A is a cross-sectional view schematically illustrating a high index contrast waveguide comprising a thin silicon core region disposed on a silicon dioxide layer and an exemplary field pattern of the fundamental optical mode supported by the waveguide.
FIG. 1B is an exemplary dispersion diagram comprising a plot of the effective index (unitless) versus the free space wavelength (in micrometers) for the waveguide shown in FIG. 1A.

A high index contrast waveguide 10 having an SOI (Silicon-on-Insulator) geometry is shown in FIG. 1A. This waveguide 10 comprises a core region 12 comprising silicon disposed on a silicon dioxide layer 14. The silicon dioxide layer 14 is cladding for the core region 12. Additional cladding 16 is disposed about the core region 12. The silicon dioxide layer 14 may be disposed on a silicon handle (not shown) comprising, e.g., a 400 or 800 micron thick silicon substrate that provides mechanical support. The silicon in the core region 12 has an index of refraction of about 3.5. The silicon dioxide has an index of about 1.43. The additional cladding may comprise polymethylmethacrylate (PMMA), which has an index of refraction of about 1.43. Other materials may also be used to fabricate the waveguide 10.

The core region 12 as well as the cladding 14, 16 may comprises different materials. The core region may comprise III-V materials in some embodiments. Other materials may also be used as well. The cladding 14, 16 may comprises, for example, other polymers. The cladding 14, 16 may also comprise nonlinear optical material or optical gain material (e.g. Er doped glass). The cladding 14, 16 may comprise materials utilized in CMOS/silicon processing as well as chemical or photo-sensitive materials. For example, the cladding 14, 16 may comprise silicon dioxide, silicon nitride, and silicon oxi-nitride in any blend, stochoimetric or non-strochiometric. The molar blend of the oxygen and nitrogen can be, for example, anywhere between 0 and 100%. Thus silicon rich, silicon dioxide, silicon nitride and oxi-nitride may be used. Low k dielectrics may also be employed. Photoresist or other materials may also be used. The cladding may comprise polyimide or carboloxide. In certain embodiments the cladding 14, 16 comprises electro-optic polymer, quantum dot composite material, nonlinear optical polymers, nonlinear optical glasses, langmuir-blodgett deposited films, or grown heterostructures. The cladding 14, 16 may comprise material responsive to biological or chemical agents, which may be utilized to fabricate a biological or chemical sensor. Still other materials, structures, and configurations are possible.

The lateral dimensions of core region 12 is about 300 to 500 nanometers (nm) and the thickness of the silicon is about 100 to 200 nm (e.g. about 120 nm) in certain embodiments, for example. The silicon dioxide layer 14 my be about 1 to 2 micrometers (μm) thick. Such dimensions provide for single mode propagation. The optical mode supported by this waveguide 10 supports is primarily polarized horizontally.

Dimensions other than those specifically recited herein are also possible. For example, dimensions outside the ranges provided can be used for different wavelengths, material systems, applications, geometries, etc.

This SOI geometry also has low waveguide loss and relatively large field concentrations outside the core region 12 of the waveguide 10. An exemplary modal concentration is shown in FIG. 1A. Contours of |E| are plotted, starting at 10% of the maximum field value at the center and incremented by 10% for each contour. Additionally, this optical mode is essentially isolated from the substrate (not shown) by the oxide layer 14, although some loss induced by tunneling leakage into the substrate may occur. An exemplary dispersion plot of the fundamental mode is shown in FIG. 1B.

Forming an electrical contact on such a waveguide 10 is particularly difficult since the waveguide is both electrically and optically isolated on all sides, e.g., by silicon dioxide and PMMA cladding 14, 16. The introduction of an electrical contact causes a significant interruption in the waveguide symmetry, which produces a large scattering loss.

Figure 2:
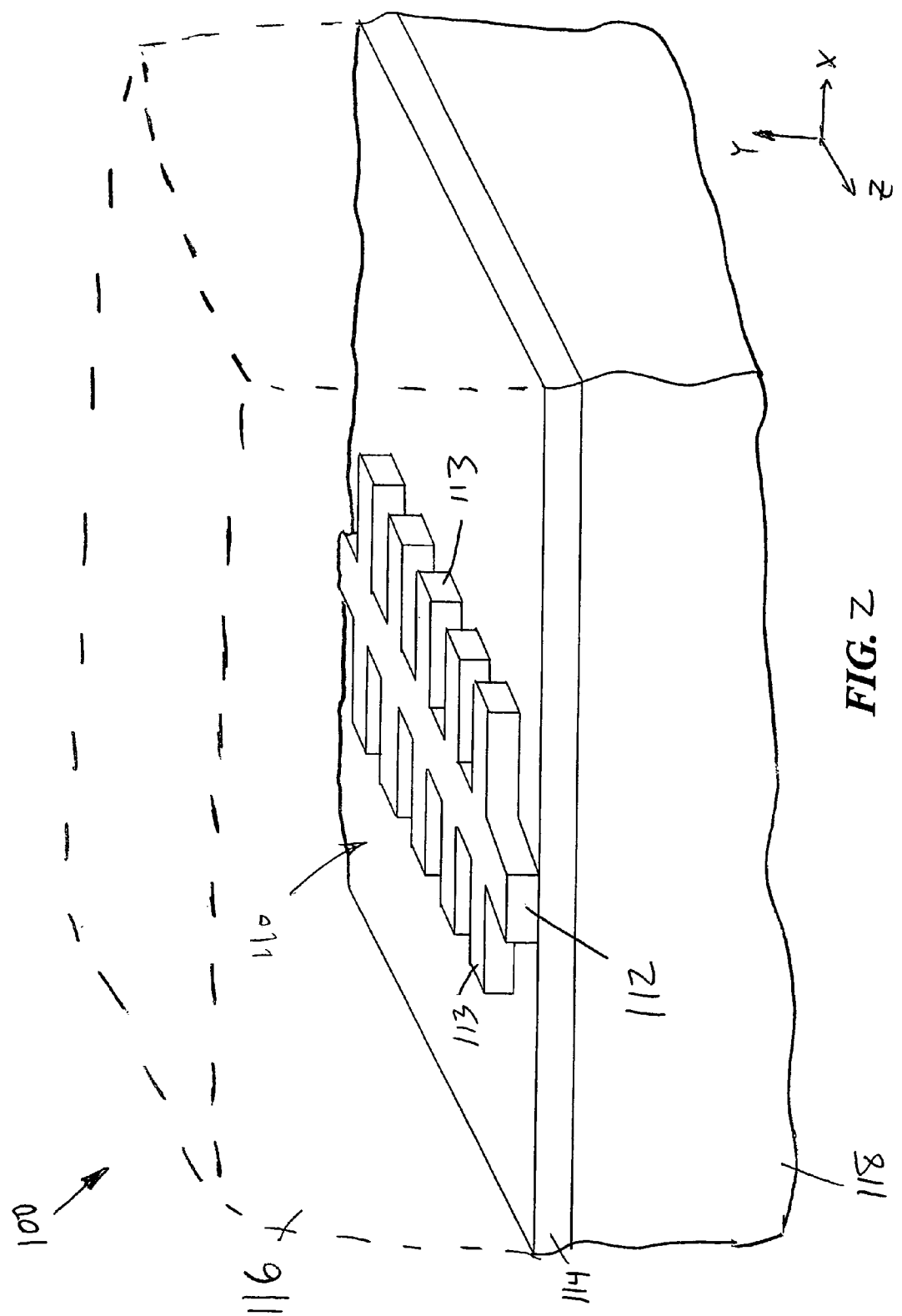
FIG. 2 is a perspective cutaway view of one embodiment of a segmented waveguide comprising a central elongate waveguide portion and a plurality of segments extending therefrom.

This problem is remedied in a waveguide structure 100 comprising a segmented waveguide 110 comprising a central elongate portion 112 (core region) and a plurality of segments 113 as shown in FIG. 2. In one embodiment, the central elongate portion 112 and the plurality of segments 113 comprises patterned silicon. The central elongate portion 112 and the plurality of segments 113 are disposed on a silicon dioxide layer 114. Cladding 116 is formed over the central elongate portion 112 and the plurality of segments 113. This cladding 116 may comprise, for example, PMMA, in some embodiments. The central elongate portion 112 and the plurality of segments 113 may be formed on a substrate 118 that provides structural support.

In other embodiments, other materials may be used. For example, the central elongate portion 112 and the plurality of segments 113 may comprise III-IV materials such as InP, GaAs, GaAlAs, InAlP, GaP, GaN. Other materials may be used instead of the layer of silicon dioxide 114 beneath the central elongate portion 112 and the plurality of segments 113. Silicon nitride and aluminum oxide (or sapphire, which is crystalline aluminum oxide) are examples of other materials that may be used. Similarly, the cladding 116 may comprise, for example, silicon dioxide, silicon nitride, or aluminum oxide. Polymers including electro-optic polymers may be used for the cladding 114, 116. Glasses, including luminescent glasses such as doped glasses like Er doped glass may also be employed. Accordingly, the cladding 114, 116 may comprise nonlinear optical material or optical gain material. The cladding 114, 116 may comprise materials utilized in CMOS/silicon processing as well as chemical or photo-sensitive materials. For example, the cladding 114, 116 may comprise silicon dioxide, silicon nitride, and silicon oxi-nitride in any blend, stochoimetric or non-strochiometric. The molar blend of the oxygen and nitrogen can be, for example, anywhere between 0 and 100%. Thus, silicon rich silicon dioxide, silicon nitride and oxi-nitride may be used. Low k dielectrics are also possible. Photoresist or other materials may also be used. The cladding may comprise polyimide or carboloxide. In certain embodiments, the cladding 114, 116 comprises quantum dot composite material, nonlinear optical polymers, nonlinear optical glasses, langmuir-blodgett deposited films, or grown heterostructures. The cladding 114, 116 may comprise material responsive to biological or chemical agents which may be utilized to fabricate a bio or chemical sensor. Still other materials, structures, and configurations are possible.

To provide increased confinement, the cladding 114, 116 around the central elongate portion 112 and the plurality of segments 113 has a lower index of refraction than the material comprising the central elongate portion. This cladding 114, 116 may also be electrically insulating.

The lateral dimensions of central elongate portion 112 may be about 300 to 500 nanometers (nm) in some embodiments. The thickness of the central elongate portion 112 and of the plurality of segments 113 may be about 100 to 200 nm (e.g. about 120 nm). The silicon dioxide layer 114 may be about 1 to 2 micrometers (μm) thick. Such dimensions provide for single mode propagation. The optical mode supported by this waveguide structure 100 is primarily polarized horizontally.

Other dimensions than those specifically recited herein are possible. For example, dimensions outside the ranges provided can be used for different wavelengths, material systems, applications, geometries, etc.

In various preferred embodiments, the waveguide structure 100 provides increased confinement. For example, the electric field of optical mode supported by the waveguide 100 may have a full-width half maximum (FWHM) that is no more than about 3.0 microns wide for certain materials systems and certain wavelengths. The FWHM of the optical mode for other materials and wavelengths may be outside this ranges. In certain embodiments, for instance, the electric field of optical mode supported by the waveguide 100 may have a full-width half maximum (FWHM) that is no more than about two times the wavelength of the optical mode. Values outside this range are also possible. The central elongate portion 112 and the surrounding cladding 114, 116 may have an index contrast of at least about 1.0 or at least about 2.0 to provide such increased confinement. This level of confinement greatly exceeds the confinement provided by other low index contrast material systems such as systems based on III-V materials. The level of confinement also greatly exceeds the confinement provided by optical fibers, which also have low index contrast. The optical modes in these low index contrast systems have FWHM intensities substantially larger than 3.0 microns wide.

High index contrast systems such as described herein that confine the optical mode to reduces dimension, however, are difficult to model as discussed more fully below. Special techniques are employed to characterize and design these high index contrast waveguides.

In particular, the modes of such a structure cannot be solved using the standard perturbative approach used for the design of low-index-contrast reflectors. For structures constructed with an array of low-index-contrast sections (e.g., arranged to form a Bragg reflector), the assumption is made that the mode distribution in both the high- and low-index regions is substantially the same. This assumption, however, does not hold for high index contrast segmented waveguides such as described herein. The modes of such a structure, however, can be solved using a Hermetian eigensolver in three dimensions, with the unit cell being a full period of the segmented waveguide (a portion of straight waveguide and a portion of waveguide with segment added). The eigensolver can be based on a finite-difference approach, although other techniques are possible. Surprisingly, high index contrast segmented waveguides can exhibit relatively low loss guiding.

The waveguide 100 may be fabricated using semiconductor processing techniques well known in the art. For example, for embodiments wherein the central elongate portion 112 and the plurality of segments 113 comprise silicon disposed on the silicon dioxide layer 114, a SOI wafer comprising a layer of silicon formed on a layer of silicon dioxide may be used. The layer of silicon can be patterned to form the central elongate portion 112 and the plurality of segments 113. The plurality of segments 113 can be lithographically defined during the same lithographic step as the etch defining the central elongate waveguide portion 112. The silicon can be etched down to the silicon dioxide layer 114. The additional cladding 116 can be deposited on the central elongate portion 112 and the plurality of segments 113. Other methods both well known in the art as well as those yet to be devised may be employed to fabricate the waveguide structure 100.

Figure 3:
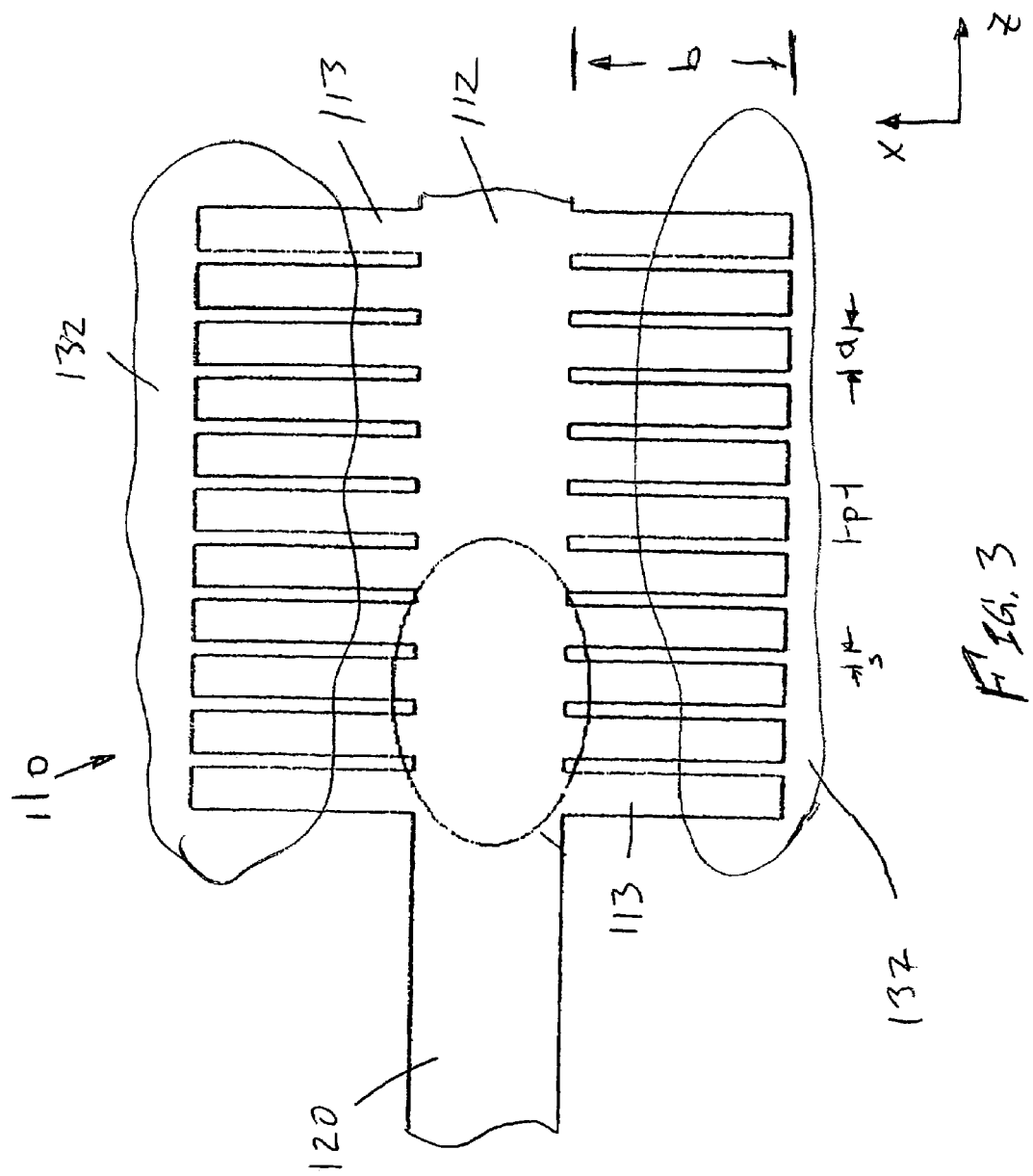
FIG. 3 is a plan view of the segmented waveguide of FIG. 2 butt coupled to a non-segmented waveguide.

A non-segmented waveguide portion 120 is shown coupled to the segmented waveguide section 110 in FIG. 3. The non-segmented waveguide portion 120 may be similar to the waveguide structure 10 depicted in FIG. 1A and discussed above with reference to FIGS. 1A and 1B. The segmented waveguide portion 110 may be similar to the waveguide structure 100 in FIG. 2.

Electrical contacts 132 are formed with the plurality of segments 113. In the embodiment shown, the segments 113 are on opposite sides of the central elongate waveguide portion 112 as are the electrical contacts 132. The electrical contacts 132 may comprise metallization, polysilicon, salicide, or other conductive material. The plurality of segments 113 may be doped.

The central elongate waveguide portion 112 may also be doped or may be undoped. The doping across in the central elongate waveguide portion 112 and for the plurality of segments 113 on opposite sides thereof may be different to produce different effects. For example, opposite doping may be used to create carrier accumulation or depletion in the central elongate waveguide portion 112 to alter the index of refraction with applied voltage across the pair of contacts 132. The device may therefore have a pn, pin, or other type of junction. In certain embodiments, the central elongate waveguide portion 112 comprises undoped semiconductor such that application of a voltage to the electrical contacts 132 induces a current to flow across the undoped semiconductor thereby heating the central elongate portion and altering the index of refraction therein. Controlled variation of the index of refraction by introducing changes in the free carrier concentrations using electrical fields and by heating is described in U.S. Pat. No. 6,834,152, filed Sep. 2, 2002 and entitled "STRIP LOADED WAVEGUIDE WITH LOW-INDEX TRANSITION LAYER" as well as U.S. Pat. No. 6,839,488 entitled "TUNABLE RESONANT CAVITY BASED ON THE FIELD EFFECT IN SEMICONDUCTORS" filed Sep. 10, 2002, both of which are incorporated herein by reference in their entirety.

The electrical contacts 132, however, are laterally disposed with respect to the central elongate portion 112 and are substantially removed from optical mode propagating therein. Optical absorption otherwise introduced by electrical contacts comprising, for example, metallization, polysilicon, salicide, and other optically absorbing electrically conductive material, is thereby reduced. Scatter loss introduced by disposing a contact feature in close proximity to the waveguide is substantially avoided by forming the contact feature from the plurality of segments 113 that induces coherent scattering like a grating. The plurality of segments 113 can be designed to produce coherent scattering that reduces coupling loss from the non-segmented waveguide 120 to the segmented waveguide 110 and reduced propagation loss in the segmented waveguide.

Accordingly, the electrical contact is formed using a lateral grating. The optical properties of this geometry are strongly dependent on the periodicity and duty cycle of this grating. This periodicity may be on the order of the wavelength of the mode supported by the waveguide structure 100. In certain preferred embodiments, this period may be between about 0.1 to 1, 2, 3, 5 or 10 times the wavelength of the optical mode supported by the waveguide structure 100. In certain embodiments, for example, the period is about 1.0 micron or less. However, the dimensions can depend, for example, on the wavelength, the materials, and the geometry, etc. Accordingly, these dimensions are not limiting and periods outside these ranges may be more desirable for different designs and applications. The duty cycle is ratio of the width, a, of the segments to the period, p, of the segments. Thus, for a grating having a duty cycle of 0.7 and a period of 1 μm, the width of the segments are 0.7 μm long. In theory, the segments 113 comprising silicon strips in FIG. 2 can have a length, b, that is large. However, for properly chosen periodicities, the segments 113 can be terminated after a relatively short isolation distance.

Surprisingly, however, high index contrast segmented waveguides that exhibit relatively low loss guiding are possible. If a low loss, propagating optical mode exists for a particular design, both lateral electrical contacts to the waveguide structure 100 and low loss optical guiding can be achieved. Special techniques, however, are used to model and design such high index segmented structures. Unlike for low index contrast structures, the assumption cannot be made that the mode distribution in both the high- and low-index regions is substantially the same. Nevertheless, in certain embodiments of the invention, waveguide structures 100 can be designed by calculating the Bloch modes of the segmented waveguides 110, e.g., with the aid of Bloch's theorem. The analysis begins with solution of the current and charge free Maxwell's equations $$\nabla \times \frac{1}{n(r)^2} \nabla \times H = \frac{w^2}{c^2} H \quad (1)$$

for these geometries using eigenvalues; see, e.g., J. D. Joannopoulos, R. D. Meade, and J. N. Winn, *Photonic Crystals* (Princeton Univ. Press, Princeton, 1995), which is incorporated herein by reference in its entirety. In Equation (1), n(r) is the index of refraction as a function of position, r, H is magnetic field, w is optical frequency and c is the speed of light. The H field can be the field variable, since the eigenvalue equation is in such a case Hermetian and is not generalized. Non-hermetiaan (generalized) eigenvalue equations are extremely difficult to solve, whereas Hermetian eigenvalue equations can be solved with intensive mathematical calculations.

As shown in FIGS. 2 and 3, x and y are the transverse cross-sections of the waveguide structure 100, while z is the direction of propagation. For a non-segmented waveguide 120, such as shown in FIG. 1, n(r) is generally the same along the z direction. In the case of the segmented waveguide 110, n(r) is periodic such that n(r+Δz)=n(r), where Δz is the period, p. Utilizing Bloch's theorem in the propagation direction, all the eigenvectors of Equation (1) may be written in the form:

$$\Psi(w)=\phi(r)\exp(i\beta z) \quad (2)$$

where Ψ(w) is an eigenvector corresponding to a particular choice of w, β is the crystal lattice vector, and φ(r) is the local field distribution in a unit cell (a 3-vector). The propagating modes of a segmented waveguide 110 will be among the solutions to (2).

In order to solve this problem for complex structures, the index of refraction distribution of the structure is discretized. Many approaches are available. For example, the Finite-Difference Time Domain (FDTD) grid can be used as the basis of the discretization, since such an approach implicitly enforces the appropriate continuity and divergence conditions; see, e.g., A. Taflove and S. C. Hagness, *Computational Electrodynamics* (Artech, Boston, 2000), which is incorporated herein by reference in its entirety. The linear system results in a large sparse matrix equation, with about 0.6 million variables for a given exemplary calculation using a discretization of 0.02 μm. The lowest nonzero eigenvalues can nevertheless be found with the suitable choice of iterative methods; see, e.g., G. H. Golub and C. F. Van Loan, *Matrix Computations* (The Johns Hopkins University Press, Baltimore, 1996), which is incorporated herein by reference in its entirety. The modes generated using a direct solver can be identical to the modes generated by a large FDTD simulation with a long runway (e.g., tens or hundreds of microns of real space for a wavelength of about 1550 nm) and can be substantially faster to generate.

In certain preferred approaches, Equation (1) remains Hermetian in whatever set of boundary conditions are chosen for the unit cell. The z boundary condition for a unit cell calculation is periodic with the appropriate Bloch factor. A zero-field boundary conditions can be imposed on the edge of the unit cell in x and y, corresponding roughly to having a perfect conductor in this region. Such boundary conditions do not correspond to the actual design; however, for solutions to Equation (1) that reduce close to zero at these boundaries, the introduction of this spurious conductor should not disturb the eigenvalue or vector.

An effective index for the Bloch modes can be defined as the β/w. With a choice of effective indices in the range of 1 to 4 for cells of periodicity of about 0.3 μm, the lowest frequency eigenvalues can be calculated to be the fundamental propagating optical mode that has wavelengths in free space in the range of about 1-2 μm for certain non-limiting embodiments. Thus, although not true for some embodiments, solving for the modes of interest involves obtaining the lowest eigenvalue of the system for varying P values. In general, however, solving Equation (1) with functions of the form Equation (2) will produce a series of frequencies, a portion of which will be in the range of physically meaningful solutions. In certain cases, useful data will be obtained for higher values in the eigenspectrum. A dispersion diagram for the Bloch modes of a given segmented waveguide 110 design can be generated using the effective index defined as above.

As an example, one embodiment of a segmented waveguide structure 100 with periodicity 0.28 um and a duty cycle of 0.5 supports a fundamental Bloch mode. An exemplary dispersion diagram showing the dispersion in both the non-segmented and segmented waveguides 120, 110 is presented in FIG. 4A. The plot for the segmented waveguide 110 is for an (x-y) plane through the middle of a segment.

Figure 4:
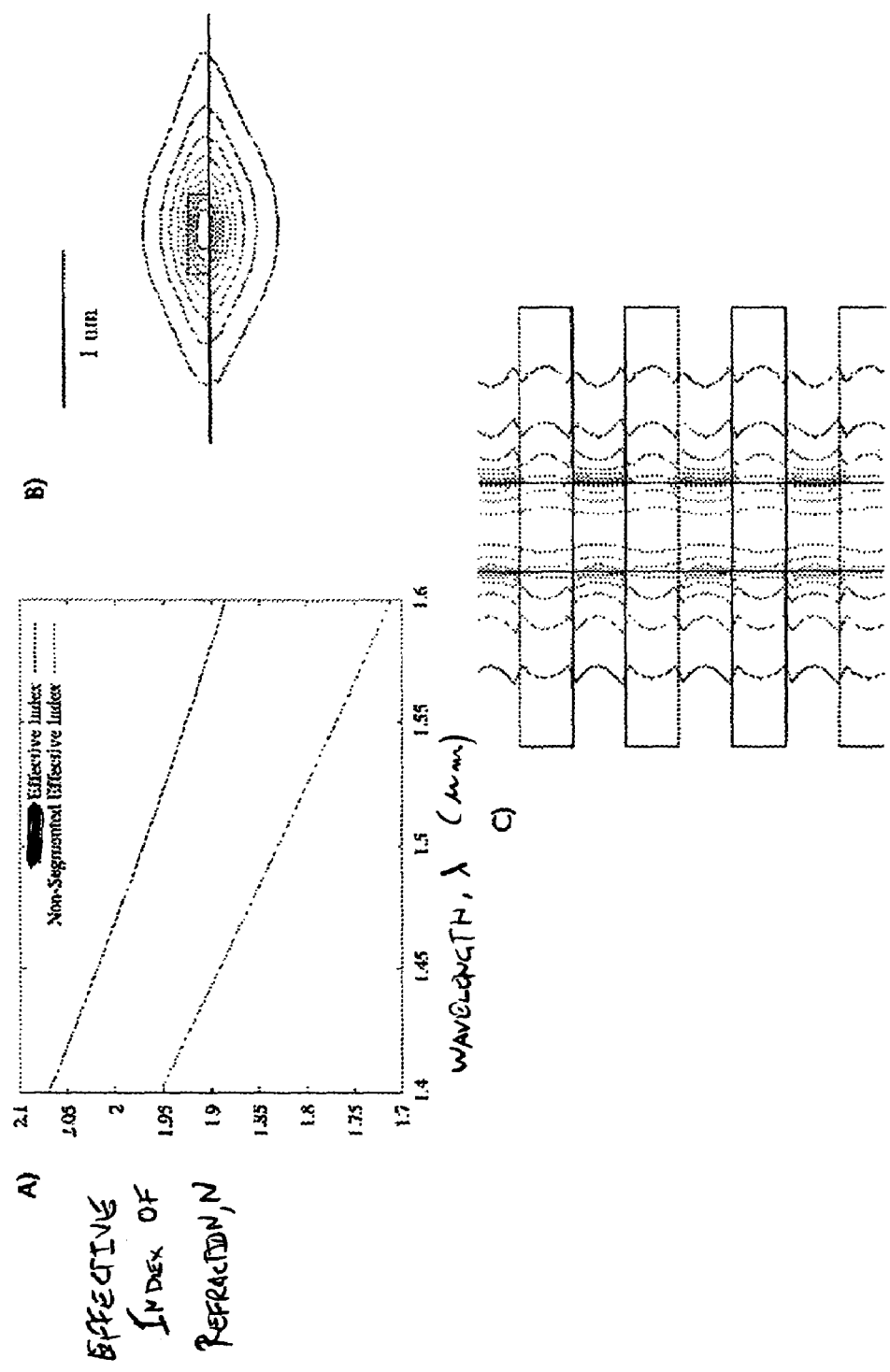
FIG. 4A is an exemplary dispersion diagram of both the segmented waveguide and the non-segmented waveguides.
FIG. 4B is a cross-sectional schematic illustration of the segmented waveguide showing an exemplary modal pattern of a Bloch mode.
FIG. 4C is cross-sectional view through the central elongate waveguide portion and the plurality of segments that includes a plot of an exemplary modal pattern of the Bloch mode.

The dispersion plot in FIG. 4A shows the effective index of the Bloch mode in the segmented waveguide 110 closely matching that of a non-segmented waveguide 120. Accordingly, little insertion loss results from index mismatch if light is coupled from the non-segmented waveguide 120 into the segmented waveguide 110. Moreover, the region of 1550 nm for this waveguide has little dispersion. Small dispersion levels may not always be present. For many periodicities, the segmented waveguide can have band-gaps with high back-reflection and prevent the forward propagation of particular frequencies altogether. In the region of such behavior, the dispersion diagram might exhibit a derivative dw/dβ approaching zero.

A transverse cross-sectional view showing an exemplary plot of E field intensity in the waveguide structure is presented in FIG. 4B. The contours of |E| are plotted, starting at 10% of the maximum value at the center and with contour increments of 10%. Similarly, a longitudinal cross-sectional view showing an exemplary plot of E field intensity in the waveguide structure is presented in FIG. 4C. This cross-section bisects the central elongate waveguide portion 112 and the plurality of segments 113 into two equal upper and lower halves. Four periods of the waveguide segments 113 are shown for illustrative purposes.

As shown in FIGS. 4B and 4C, for the periodicity selected, the field amplitudes can be small at the edges of the waveguide domain. Certain choices of periodicity may not exhibit this behavior and will have higher radiative losses. Accordingly, in certain preferred embodiments, the segmented region 110 is designed to ensure low losses. Because the mode exhibits low loss in this geometry, the segments 113 need not be extend to infinity. In certain preferred embodiments, however, the segments are longer than several e-folding lengths of the field (e.g., the distance wherein the field decrease by several 1/e multiples) to prevent the optical mode from being influenced by the end of the lateral segments. For various embodiments, the segments extend 2000 nm in the lateral direction (±x direction) from the center of the segmented waveguide 110. Other sizes are possible, for example, for different material systems, operating wavelengths, configuration and designs, and/or applications, etc.

Figure 5:
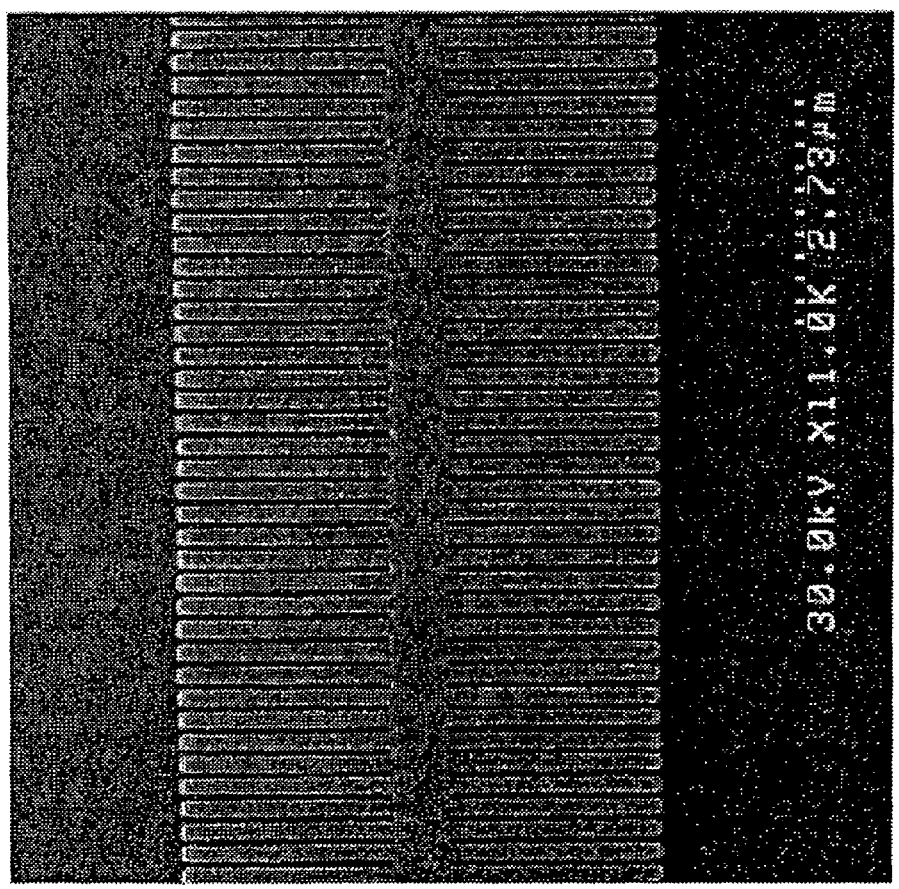
FIG. 5 a scanning electron micrograph of one embodiment of a segmented waveguide such as shown in FIGS. 2 and 3.

FIG. 5 shows a scanning electron micrograph of an exemplary device. Such a device was fabricated using electron beam lithography. This fabrication process exemplary and other processes may be employed. For example, industry standard processing steps (e.g., CMOS/silicon processing) may be used, especially for mass producing products. Different processing steps may be used for different material systems and different designs and applications. Fabrication processes both well known in the art as well as those yet to be devised may be used.

Figure 6:
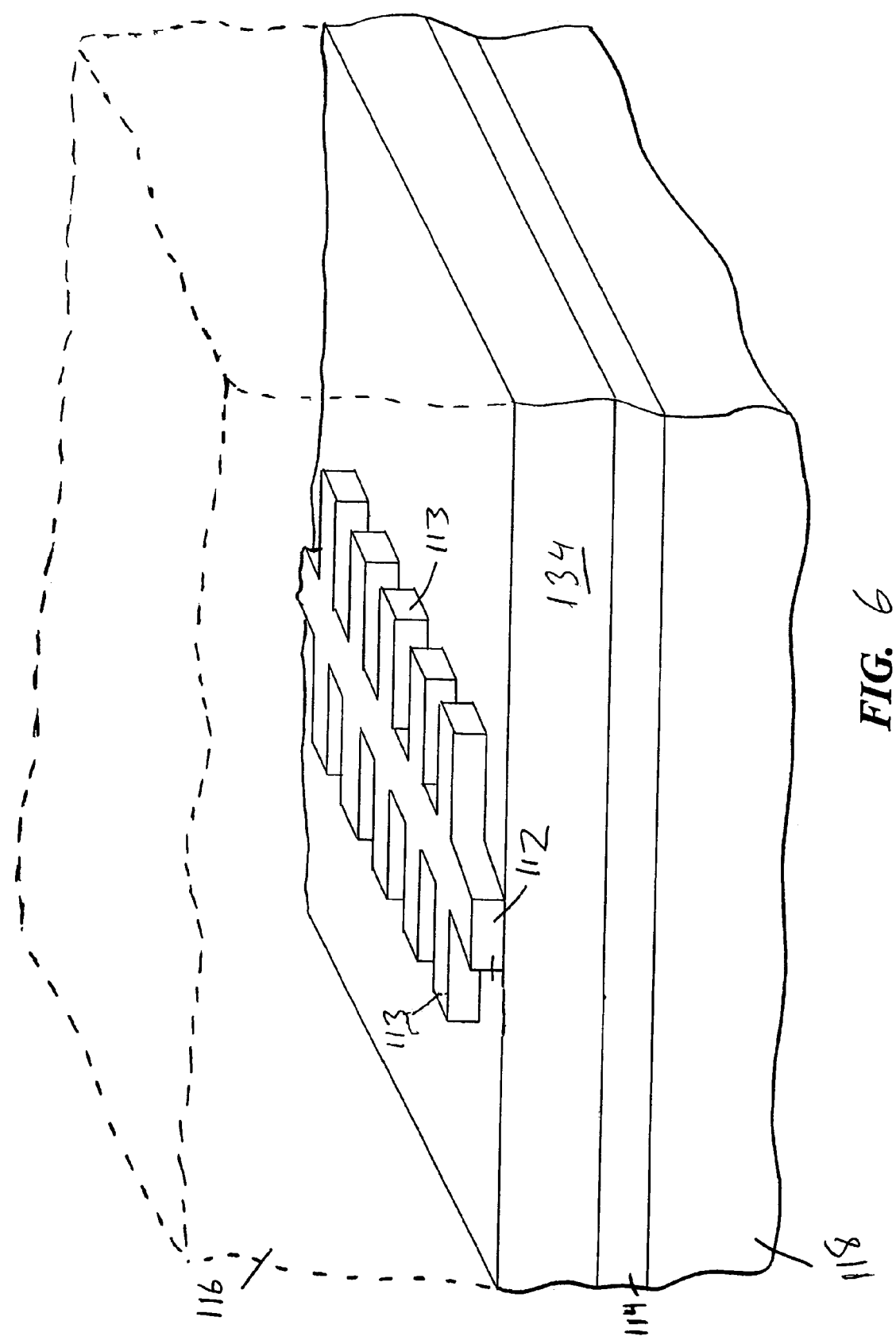
FIG. 6 is a perspective cutaway view of one embodiment of a strip-loaded segmented waveguide.

As discussed above, the embodiments of the invention are not limited to those specifically described herein. A wide range of variation in design is possible. For example, the waveguide structure 100 may comprise a strip loaded waveguide such as shown in FIG. 6. A slab 134 may be disposed between the elongate waveguide portion 112 and the underlying layer of silicon dioxide 114. The optical mode can be propagated within the elongate waveguide portion 112 and a portion of the slab 134 in proximity to the central elongate waveguide portion. A variety of materials may be used to construct such a device.

Figure 7:
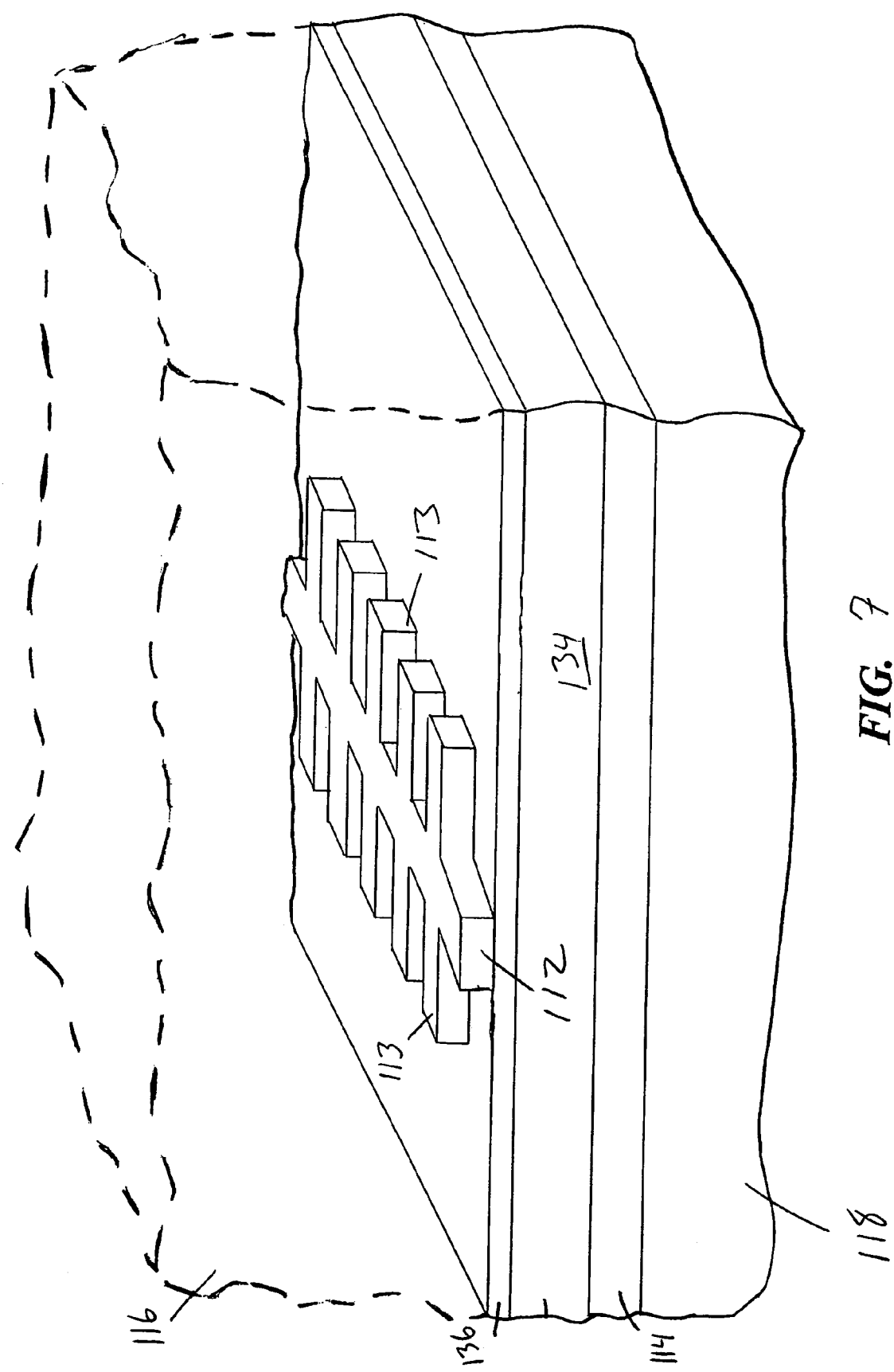
FIG. 7 is a perspective cutaway view of one embodiment of a strip-loaded segmented waveguide with a low index translation layer.

The waveguide structure 100 may alternatively comprise a strip loaded waveguide with a low index transition region 136 disposed between the elongate waveguide portion 112 and the slab 134 such as shown in FIG. 7. The optical mode can be propagated within the elongate waveguide portion 112 and the portion of the slab 134 in proximity thereto despite the presence of the low index transition region. See, e.g., U.S. Pat. No. 6,834,152, filed Sep. 2, 2002 and entitled "STRIP LOADED WAVEGUIDE WITH LOW-INDEX TRANSITION LAYER" cited above. This low index transition region, may comprise, e.g., silicon dioxide. The central elongate waveguide portion 112 and the plurality of segments 113 as well as the slab 134 may comprise, for example, silicon in some embodiments. Other materials may also be used.

Figure 8:
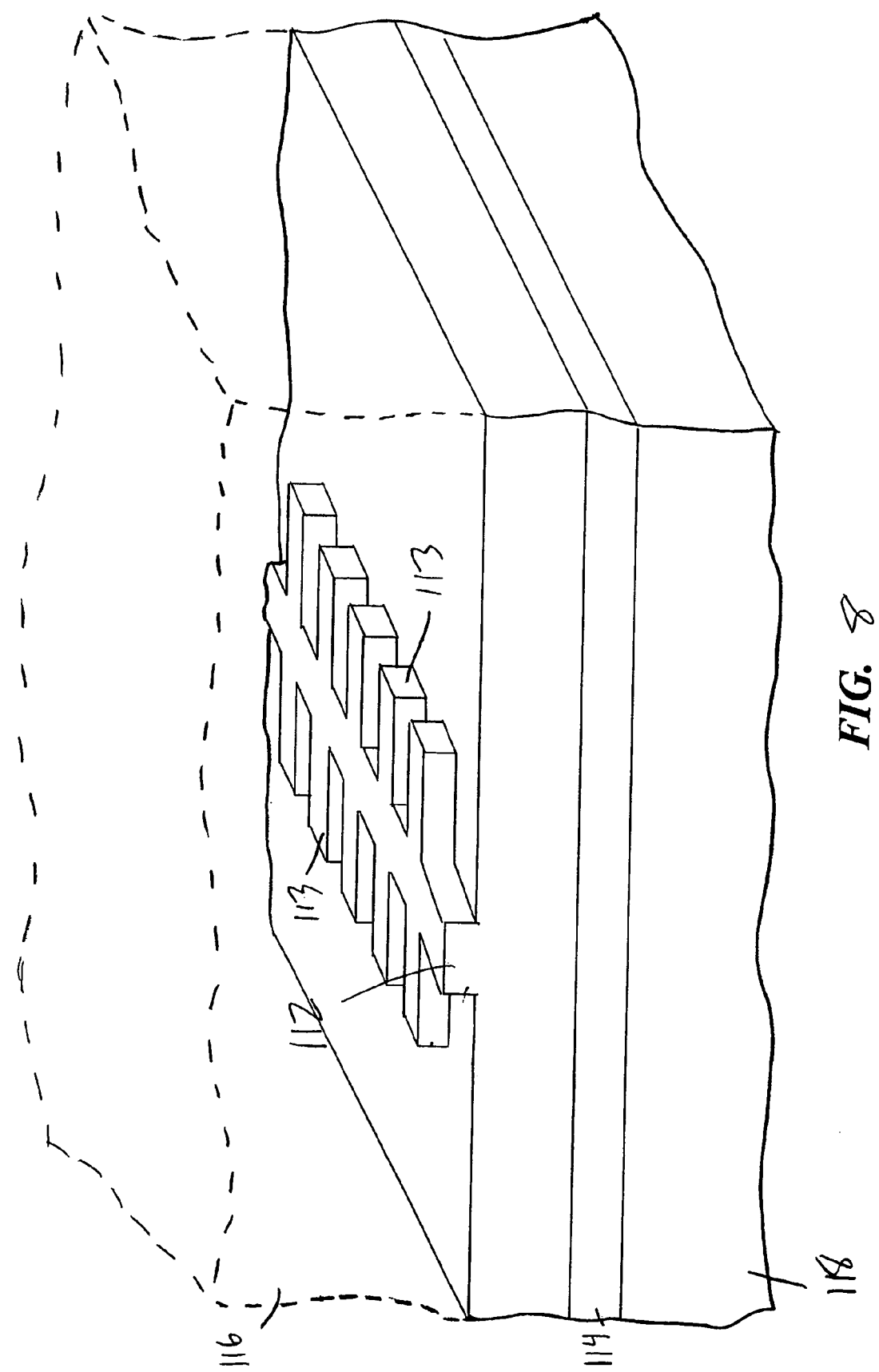
FIG. 8 is a perspective cutaway view of one embodiment of a rib or ridge segmented waveguide.

In other embodiments, the waveguide structure 100 may comprise a ridge or rib waveguide such as shown in FIG. 8. In certain embodiments, for example, the central elongate waveguide portion 112 and plurality of segments 113 are not etched down to the silicon dioxide layer 114 such that a ridge waveguide is formed in the silicon above the silicon dioxide layer 114. As described above, other materials may also be used.

Figure 9:
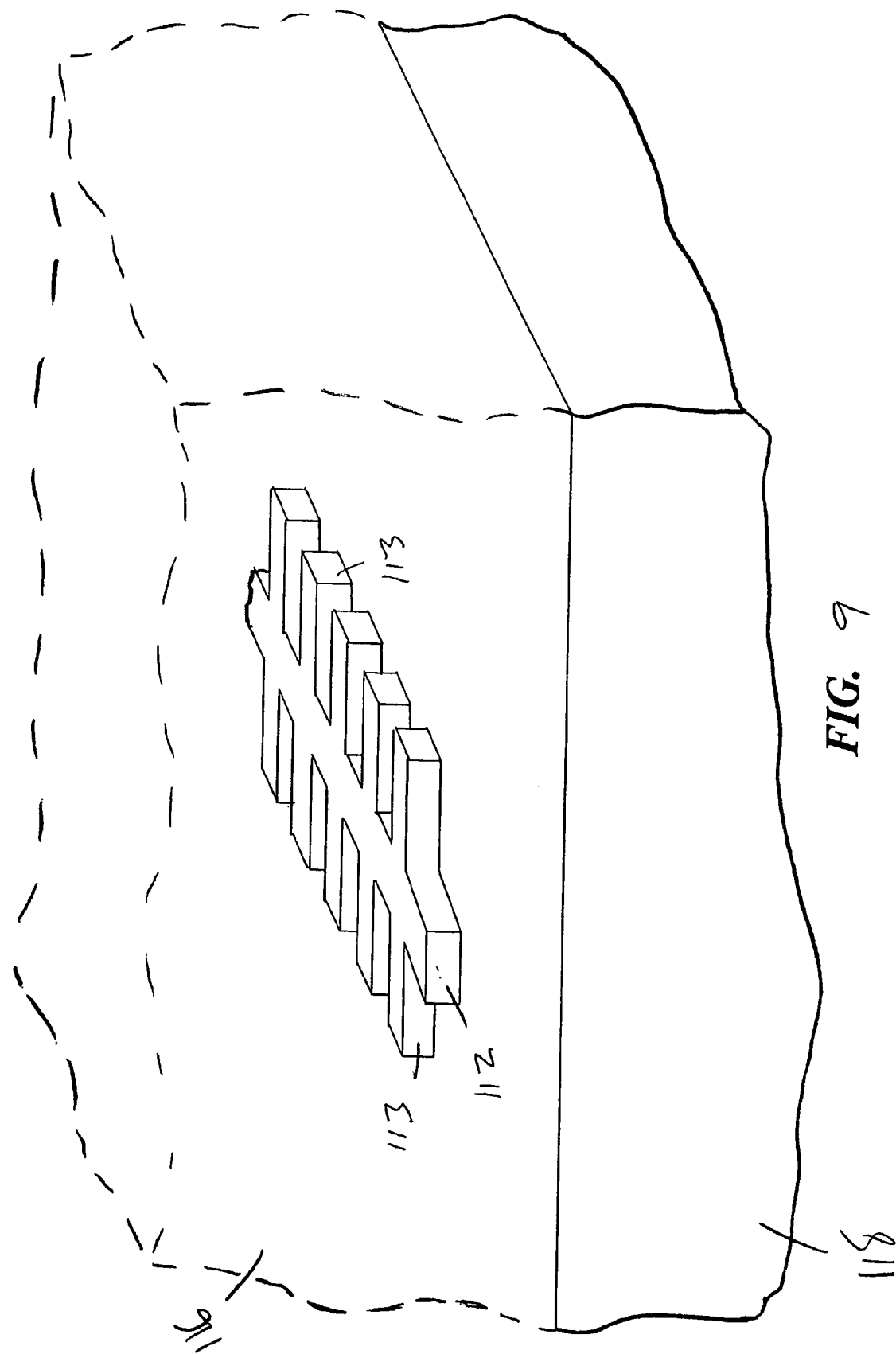
FIG. 9 is a perspective cutaway view of one embodiment of a channel segmented waveguide.

In other embodiments, the waveguide structure 100 may comprise a channel waveguide such as shown in FIG. 9. In certain embodiments, for example, the central elongate waveguide portion 112 and plurality of segments 113 are disposed in a cladding such as the cladding 116. This cladding 116 may substantially surround the central elongate waveguide portion 112 and plurality of segments 113. As described above, other materials may also be used.

As described above, dimensions other than those specifically recited herein are also possible. For example, dimensions outside the ranges provided can be used for different wavelengths, material systems, applications, geometries, etc.

A wide range of other variations and configurations are possible. As described above, the dimensions and materials may vary. Additional layers and other features may be added, removed, interchanged, or moved. Different shapes are possible. Although rectangular cross-sections of the waveguides portions are shown, other cross-sectional geometries are possible. Also, although a straight linear path along the z direction is shown for the waveguide structure 100, the waveguide may follow other paths. The waveguide structure 100, may for example bend and turn, split or merge with other waveguides or devices. The segments 113 can also have different shapes. The segments can bent, taper, or have different cross-sectional shapes. The number of segments 113 is not limited. Nor is the size, spacing or periodicity of the segments 113 limited. The segments 113 need not be symmetric about the central elongate waveguide portion 112. Still other variations in the segments 113 and configuration of the waveguide structures 100 are possible.

Accordingly, high index contrast segmented waveguide geometries can support relatively low loss optical modes yet providing high confinement relative to low index contrast geometries. Moreover, these modes can be readily coupled from non-segmented waveguides 120, exhibiting low loss for simple butt-coupling. This feature will enable segmented waveguides 110 to offer viable options for electrically contacting optical waveguides in a single layer structure that supports a single optical mode with high confinement.

The waveguide structures 100 may be employed, for example, in chemical or biological sensors as well as for electro-optic and luminescent devices. In certain embodiments, chemicals or biological materials interact with the cladding thereby affecting the propagation of light propagating through the waveguide, which can be sensed. The waveguides can be clad with optically active materials, which provide large nonlinear ($\chi^2$ or $\chi^3$) optical coefficients. The waveguides can also be coated with a material that provides gain, or that changes index of refraction or dispersion when exposed to an external stimulus. Such a stimulus may, for example, be electrical, thermal, chemical, or biological. Waveguides can be clad with electro-optic polymers, polymers exhibiting large $\chi^3$ moments, liquid crystals, or electo-luminescent material such as Er doped glass. The functionalization material in such devices may reside in the waveguide cladding 114, 116 and a large modal overlap and the increased field concentrations in the deposited cladding layer enhances these effects. Other types of devices may also benefit from such designs.

Segmented waveguides 110, however, may be utilized for other applications as well. For instance, the segmented waveguides 110 could be employed as low loss frequency filters as the gratings are particularly wavelength selective.

The plurality of segments 113 can be designed to propagate the desired wavelength and to introduce loss for wavelengths not desired to be propagated. Additionally, because the optical modes in these waveguides were supported in a broadband pattern, such a configuration might be useful in isolating a signal band from a pump wavelength in an optical system. The waveguides structures 100 may also comprise mode expanders. The periodicity of segments 113 can be varied to control the dispersive properties of the waveguide and manipulate the mode shape. See, e.g., Z. Weissman and A Hardy, "2-D Mode Tapering Via Tapered Channel Wave-Guide Segmentation," Electronics Letters 28, 151401516 (1992), which is incorporated herein by reference in its entirety. Other application are also possible.

Those skilled in the art will appreciate that the methods and designs described above have additional applications and that the relevant applications are not limited to those specifically recited above. Also, the present invention may be embodied in other specific forms without departing from the essential characteristics as described herein. The embodiments described above are to be considered in all respects as illustrative only and not restrictive in any manner.

What is claimed is:

1. A waveguide structure for supporting an optical mode having a wavelength, $\lambda$, comprising:
   an elongate waveguide portion comprising doped semiconductor;
   a plurality of segments extending laterally from said elongate waveguide portion, wherein the plurality of segments comprises conductive material and has a width that is at least twice a width of the elongate waveguide portion;
   at least one electrical contact formed on a top surface section of the plurality of segments to provide electrical contact to the elongate waveguide portion through the top surface section of the plurality of segments, wherein the electrical contact is laterally disposed with respect to the elongate waveguide portion and is configured to be substantially removed from the elongate waveguide portion and the supported optical mode propagating in the elongate waveguide portion; and
   cladding disposed about said elongate waveguide portion, wherein said plurality of segments has a periodicity on the order of said wavelength, $\lambda$.

2. The waveguide structure of claim 1, wherein said plurality of segments has a periodicity between about 0.1 and 3 times said wavelength, $\lambda$.

3. The waveguide structure of claim 2, wherein said plurality of segments has a periodicity between about 0.1 and 2 times said wavelength, $\lambda$.

4. The waveguide structure of claim 1, wherein said cladding and said elongate waveguide portion have an index contrast at least about 1.0.

5. The waveguide structure of claim 2, wherein said cladding and said elongate waveguide portion have an index contrast at least about 2.0.

6. The waveguide structure of claim 1, wherein said waveguide structure has sufficiently high index contrast such that said supported optical mode has a full width half maximum intensity having a lateral dimension of about twice said wavelength, $\lambda$, or less.

7. The waveguide structure of claim 6, wherein said waveguide structure has sufficiently high index contrast such that said supported optical mode has a full width half maximum intensity having a lateral dimension of about 3 micrometers wide or less.

8. The waveguide structure of claim 1, wherein said elongate waveguide portion and said cladding comprise silicon-based materials.

9. The waveguide structure of claim 1, wherein said elongate waveguide portion further comprises a pn junction.

10. The waveguide structure of claim 1, wherein said elongate waveguide portion comprises silicon.

11. The waveguide structure of claim 10, wherein said cladding comprises silicon dioxide, silicon nitride, or silicon oxinitride.

12. The waveguide structure of claim 1, wherein said cladding comprises nonlinear optical material, optical gain material, or material responsive to chemical or biological agents.

13. The waveguide structure of claim 1, wherein said cladding comprises polymer or low k dielectrics.

14. The waveguide structure of claim 1, wherein said cladding comprises electro-optic polymer, quantum dot composite material, nonlinear optical polymer, nonlinear optical glass, a langmuir-blodgett deposited film, or a grown heterostructure.

15. The waveguide structure of claim 1, wherein said cladding comprises PMMA, polyimide, carboloxide, or Er doped glass.

16. The waveguide structure of claim 1, wherein said plurality of segments comprise silicon, gallium arsenide, gallium phosphide, gallium nitride, indium phosphide, or gallium aluminum arsenide.

17. The waveguide structure of claim 1, wherein said plurality of segments are doped semiconductor.

18. The waveguide structure of claim 1, wherein said plurality of segments comprise:
    a first plurality of segments extending from a first side of said elongate waveguide portion; and
    a second plurality of segments extending from a second side of said elongate waveguide portion.

19. The waveguide structure of claim 18, wherein first and second electrical contacts are formed with said first and second plurality of segments, respectively.

20. The waveguide structure of claim 19, wherein said first and second electrical contacts comprises metallization, salicide, or polysilicon.

21. The waveguide structure of claim 1, further comprising a substrate over which said elongate waveguide portions, said plurality of segments, and said cladding are disposed.

22. The waveguide structure of claim 21, wherein said substrate comprises silicon or glass.

23. The waveguide structure of claim 1, wherein said elongate waveguide portion supports a single optical mode.

24. A waveguide structure for supporting an optical mode having a wavelength, $\lambda$, comprising:
    an elongate waveguide portion;
    a plurality of segments extending laterally from the elongate waveguide portion, wherein the plurality of segments has a width that is at least twice a width of the elongate waveguide portion;
    at least one electrical contact formed on a top portion of the plurality of segments to provide electrical contact to the elongate waveguide portion through the top portion of the plurality of segments, wherein the electrical contact is laterally disposed with respect to the elongate waveguide portion and is substantially removed from the elongate waveguide portion and an optical mode propagating in the elongate waveguide portion; and
    cladding disposed about the elongate waveguide portion.

25. The waveguide structure of claim 24, wherein the plurality of segments comprises semiconductor material.

26. The waveguide structure of claim 24, wherein the plurality of segments comprises doped silicon.

27. The waveguide structure of claim 24, wherein the elongate waveguide portion comprises doped semiconductor.

28. The waveguide structure of claim 24, wherein the plurality of segments has a periodicity on the order of the wavelength,λ.

29. A high index contrast waveguide structure for propagating a wavelength,λ, comprising:
- an elongate waveguide portion;
- a plurality of segments extending laterally from said elongate waveguide portion, said plurality of segments having periodicity so as to produce coherent scattering and reduced reflection, wherein the plurality of segments has a width that is at least twice a width of the elongate waveguide portion;
- at least one electrical contact formed with a top section of the plurality of segments to provide electrical contact to the elongate waveguide portion through the top section of the plurality of segments, wherein the electrical contact is laterally disposed with respect to the elongate waveguide portion and is substantially removed from the elongate waveguide portion and an optical mode propagating in the elongate waveguide portion; and
- cladding disposed about said elongate waveguide portion, wherein said elongate waveguide portion and said cladding have sufficiently high index contrast so as to support an optical mode having a full width half maximum intensity with a width of about twice said wavelength,λ, or less.

30. The waveguide structure of claim 29, wherein said elongate waveguide portion comprises doped semiconductor.

* * * * *

UNITED STATES PATENT AND TRADEMARK OFFICE
CERTIFICATE OF CORRECTION

PATENT NO.         : 7,315,679 B2
APPLICATION NO. : 11/146940
DATED                   : January 1, 2008
INVENTOR(S)        : Michael J. Hochberg et al.

It is certified that error appears in the above-identified patent and that said Letters Patent is hereby corrected as shown below:

On Face Page, Column 1, Line 5, item 75, Inventors delete "Altadena," and insert -- Encinitas --, therefor.

In Column 3, Line 37, delete "stochoimetric" and insert -- stoichiometric --, therefor.

In Column 3, Line 38, delete "non-strochiometric." and insert -- non- stoichiometric. --, therefor.

In Column 3, Line 55, delete "my" and insert -- may --, therefor.

In Column 4, Line 46, delete "stochoimetric" and insert -- stoichiometric --, therefor.

In Column 4, Lines 46-47, delete "non-stochiometric." and insert

-- non- stoichiometric. --, therefor.

In Column 5, Line 18, before "ranges." delete "this" and insert -- these --, therefor.

In Column 5, Line 47, delete "Hermetian" and insert -- Hermitian --, therefor.

In Column 7, Line 41 (Approx.), delete "Hermetian" and insert -- Hermitian --, therefor.

In Column 7, Line 42 (Approx.), delete "Non-hermetiaan" and insert

-- Non-Hermitian --, therefor.

In Column 7, Line 43 (Approx.), delete "Hermetian" and insert -- Hermitian --, therefor.

UNITED STATES PATENT AND TRADEMARK OFFICE
CERTIFICATE OF CORRECTION

PATENT NO. : 7,315,679 B2
APPLICATION NO. : 11/146940
DATED : January 1, 2008
INVENTOR(S) : Michael J. Hochberg et al.

It is certified that error appears in the above-identified patent and that said Letters Patent is hereby corrected as shown below:

In Column 8, Line 17, delete "Hermetian" and insert -- Hermitian --, therefor.

In Column 8, Line 35, delete "P" and insert -- $\beta$ --, therefor.

In Column 10, Line 58, delete "electo-luminescent" and insert -- electroluminescent --, therefor.

Signed and Sealed this

Fifteenth Day of July, 2008

JON W. DUDAS
*Director of the United States Patent and Trademark Office*